United States Patent [19]

Kormos et al.

[11] Patent Number: 5,682,890
[45] Date of Patent: Nov. 4, 1997

[54] MAGNETIC RESONANCE STEREOTACTIC SURGERY WITH EXOSKELETON TISSUE STABILIZATION

[75] Inventors: Donald W. Kormos, Parma; David W. Piraino, Shaker Heights, both of Ohio

[73] Assignee: Picker International, Inc., Highland Heights, Ohio

[21] Appl. No.: 378,511

[22] Filed: Jan. 26, 1995

[51] Int. Cl.$^6$ ................................. A61B 5/055
[52] U.S. Cl. ................... 128/653.2; 128/653.5; 606/130
[58] Field of Search ............ 128/653.1, 653.2, 128/653.5, 303 B; 378/205, 206, 37; 356/247, 248; 606/130

[56] References Cited

U.S. PATENT DOCUMENTS

| | | | |
|---|---|---|---|
| 4,485,819 | 12/1984 | Igl | 128/650 |
| 4,733,661 | 3/1988 | Palestrant | 128/303 B |
| 4,793,355 | 12/1988 | Crum et al. | 128/653 |
| 4,896,673 | 1/1990 | Rose et al. | 128/660.03 |
| 5,230,338 | 7/1993 | Allen et al. | 128/653 |
| 5,260,985 | 11/1993 | Mosby | 378/164 |
| 5,309,913 | 5/1994 | Kormos et al. | 128/653.1 |
| 5,370,117 | 12/1994 | McLaurin | 128/653.1 |
| 5,398,684 | 3/1995 | Hardy | 128/653.1 |
| 5,517,990 | 5/1996 | Kalfas et al. | 128/653.1 |

FOREIGN PATENT DOCUMENTS

| | | |
|---|---|---|
| 032 751A2 | 1/1981 | European Pat. Off. . |
| WO 91/04711 | 4/1991 | WIPO . |

OTHER PUBLICATIONS

"Posicast™ Thermoplastic Material For Radiation Therapy Fixation–Mask Fabrication", Sinmed BV, at least as early as Jan. 25, 1994.

"Posifix-4™ Head Positioner Carbon Fibre Support For the Head and Neck" Sinmed BV, at least as early as Jan. 25, 1994.

"Posifix-1™ Head, Neck and Shoulder Positioner Patient Positioner For Radiation Treatments to the Head, Neck and Throat", Sinmed BV, Oct. 2, 1993.

"A Computer–Assisted System for 3–D Frameless Localization in Stereotaxic MRI" Clarysse, et al. IEEE Transactions on Medical Imaging, vol. 10, No. 4, Dec. 1991.

"A Frameless, Armless Navigational System for Computer–Assisted Neurosurgery", Kato, et al. J. Neurosurg 74:845–849, May, 1991.

(List continued on next page.)

*Primary Examiner*—Marvin M. Lateef
*Assistant Examiner*—Eleni Mantis Mercader
*Attorney, Agent, or Firm*—Fay, Sharpe, Beall, Fagan, Minnich & McKee

[57] ABSTRACT

An exoskeleton material (12), such as a thermoplastic mesh, is heat softened. The heat softened material is stretched over and conformed to a soft tissue region of the patient, such as a patient's breast. The material is allowed or caused to set or harden and is affixed (14) to a patient support (10) such that the soft tissue is firmly constrained. Magnetic resonance visible markers (18) are affixed to the exoskeleton material adjacent the soft tissue. The patient is examined with a magnetic resonance imaging device (20) to generate a three-dimensional image representation (28) for display on a monitor (32). Using the markers, a wand (40) with emitters (42) receivers (44), and a coordinate system relationship processor (48) determines, a relation or transform between a coordinate system of the patient and a coordinate system of the image is determined and displayed on the monitor. A trajectory for a biopsy, resection, or the like, is planned using a guide (50). Emitters (52) on the guide are activated to generate a corresponding human-readable trajectory display through the image displayed on the monitor. After repositioning the guide as necessary, an appropriate trajectory and depth through the patient is selected from the human-readable display. An appropriate medical instrument (64) is inserted along the guide to perform the biopsy, resection, or other medical procedure.

11 Claims, 2 Drawing Sheets

OTHER PUBLICATIONS

"A Frameless Stereotaxic Operating Microscope For Neurosurgery" Friets, et al. IEEE Transactions on Biomedical Engineering, vol. 36, No. 6, Jun., 1989.

Cass Computer Assisted Stereotactic Surgery, MIDCO Medical Instrumentation and Diagnostics Corporation, advertising brochure, 1992.

"Dosimetric Properties of the Carbon Fibre Based Head Positioning System", The Netherlands Cancer Institute, (Antoni van Leeuwenhoek Huis), Jun. 1992.

MAGNETIC RESONANCE STEREOTACTIC SURGERY WITH EXOSKELETON TISSUE STABILIZATION

BACKGROUND OF THE INVENTION

The present invention relates to the stereotactic arts. It finds particular application with breast surgery and will be described with particular reference thereto. It is to be appreciated, however, that the present invention will also find application in conjunction with stereotactic procedures on other portions of the anatomy.

Three-dimensional diagnostic image data of selected regions of a human patient are commonly available with magnetic resonance imagers, CT scanners, and other medical diagnostic equipment. These imaging modalities provide structural detail with a resolution of a millimeter or better. Various stereotaxy procedures have been developed which require extreme accuracy. One of the difficulties which has arisen is accurately determining an accurate spatial correlation between the medical diagnostic image and the patient.

Stereotaxy has found particular application in neurosurgical procedures. Neurosurgery includes numerous procedures which require extreme accuracy, such as guided-needle biopsies, shunt placements, craniotomies for lesion or tumor resection, and the like. A mechanical ring or frame was attached to the patient's skull before images are taken, from which the name "framed" stereotaxy has evolved. This frame was typically attached to the patient using various mounting hardware methods that include sharp points or pins that pierce the skin and locate into the skull. The frame carried a "localizer" that includes various adjustable, but lockable hardware elements, angle indicators, and the like which enabled a surgical instrument or a guide for the surgical instrument to be mounted in a selected position relative to the patient. Due to the presence of the localizer during the diagnostic imaging, the localizer was visible in the resultant images. Hence, the relationships between the diagnostic image data, the frame, the localizer, and the patient were precisely known.

Rather than using a mechanical frame which pierced the skin, other constructions which hold the head immovably in the registered position have also been proposed. One such restraint included a base plate or support for the back of the head made of perspex acrylic. A mask of open mesh was stretched over the patient's face and rigidly affixed to the base. For accurate conformity with individual patients, the mask was configured of a thermoplastic material which could be softened in hot water, stretched or molded into conformity with the patient's face, and connected to the base plate. When the plastic mesh material was cooled it set and the patient's head was rigidly positioned.

The prior art neurosurgery frames or other restraints relied on the patient's internal skeleton, such as the skull, as an integral part of its position maintenance system. Breast tissue, lacking an internal skeleton has typically been handled differently. For x-ray mammographic examinations, the tissue has commonly been clamped between a pair of plates causing significant patient discomfort. In one technique for biopsies or resections, a stereotactic frame was associated with the plates and the radiologist inserted a probe carrying a barbed wire to the lesion or tumor to be resectioned or biopsied. Because the wire was barbed, its end would hold its position even after the plates were removed. The surgeon, in a separate procedure with the plates removed, followed the wire to the lesion or tumor. An additional problem with this technique is that the surgeons often found the wire did not define the best approach to the tumor or lesion. Generally, the plates constrained the radiologist's approaches. Moreover, the extreme distortion caused by the plates interfered with selection of the best approach.

One problem with x-ray mammography is that it has difficulty distinguishing among soft tissue types. There is a generally poor contrast between "dense" breast tissue found in about 8% of women and lesions or tumors. Scars from prior treatment are also difficult to distinguish from tumors or lesions.

Magnetic resonance is ideally suited for examining soft tissue and distinguishing among various types and conditions. However, in order to maintain an accurate registration between the soft tissue and resultant images, it has again been proposed to use non-ferrous radiographic style clamping plates. The clamping plates again have the above-described problems, whether used for radiology or magnetic resonance imaging.

The present invention provides a new and improved technique which simply and painlessly correlates the coordinate system of three-dimensional image data obtained from magnetic resonance or other diagnostic imaging sources with the coordinate system of the patient.

SUMMARY OF THE INVENTION

In accordance with one aspect of the present invention, a method of soft tissue stereotaxy is provided. A flexible material is softened, shaped, and contoured to the soft tissue region. The soft material is allowed or caused to set, forming a stiff exoskeleton and adhered to a base structure. A plurality of magnetic resonance sensitive markers are affixed to or incorporated into the exoskeleton structure. The patient along the exoskeleton and plate is positioned in a magnetic resonance imaging device and a volumetric image representation is generated. The relative position of the markers on the exoskeleton and in the images is coordinated and a stereotactic procedure is performed.

One advantage of the present invention is that it provides better access for stereotactic procedures.

Another advantage of the present invention is that it minimizes surgical trajectories and permits optimizing of surgical approaches.

Another advantage of the present invention resides in improved patient comfort.

Another advantage of the present invention is that portions of the exoskeleton which might interfere with an optimal surgical path are readily removable.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
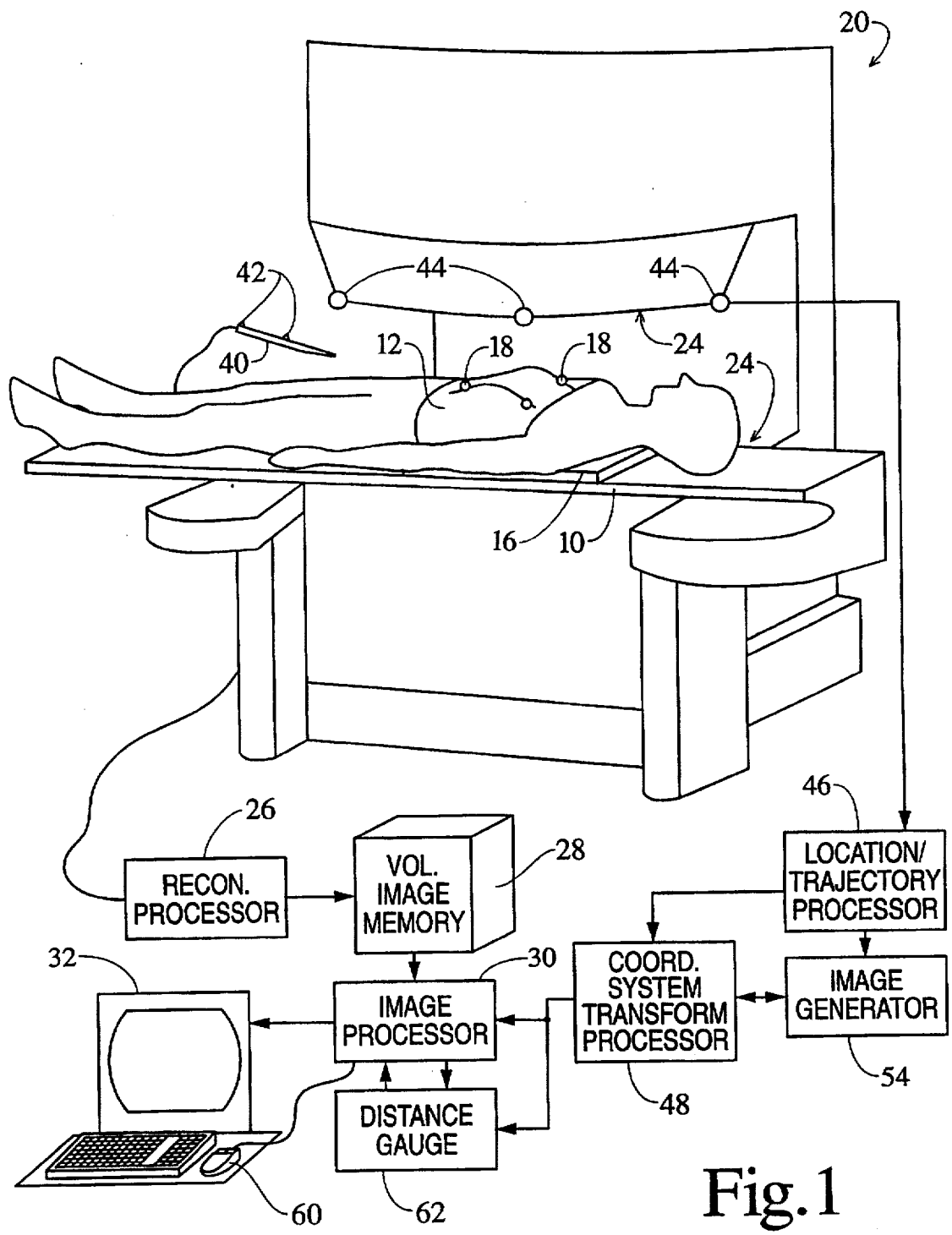
FIG. 1 is a diagrammatic illustration of a stereotaxy system in accordance with the present invention.
Figure 1A:
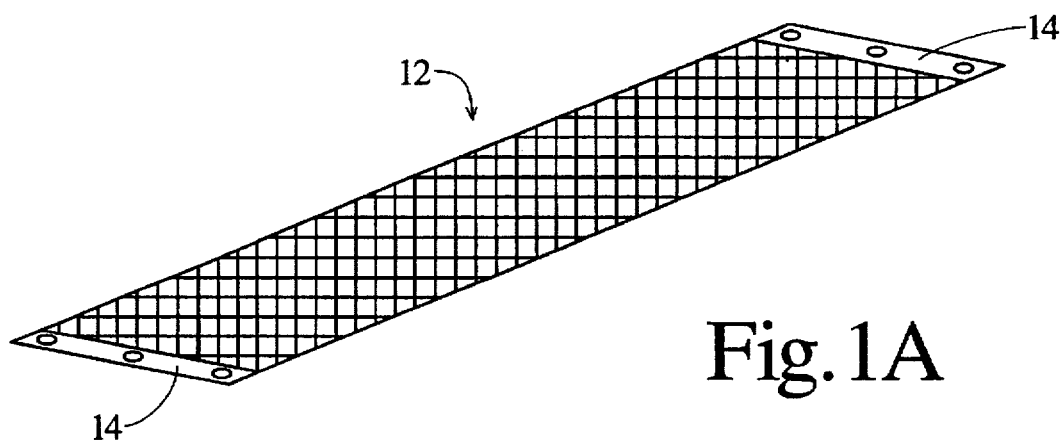
FIG. 1A is a detailed view of a sheet of the preferred exoskeleton material; and, FIG. 2 is a detailed illustration of the patient restraint and an exemplary surgical tool of the stereotaxy system of FIG. 1.

With reference to FIG. 1, a patient is received on a patient support 10. A rectangular sheet of an exoskeleton material 12 (FIG. 1A) is temporarily softened to become flexible and stretchable. In the preferred embodiment, the exoskeleton material is a mesh of a thermoplastic material which softens at temperatures of about 70° C. The material is held or immersed in hot water until soft. The flexible sheet is then removed from hot water and allowed to cool to about body temperature. The material is then stretched over and molded to the soft tissue region and affixed by clamps or other affixing means 14 to sides of the patient support. Optionally, a base 16 is provided between the patient support and the patient to which the exoskeleton 12 is affixed. Thereafter, the mesh material is allowed or caused to set to a relatively rigid state. With the thermoplastic material of the preferred embodiment, the material sets as it cools. However, setting may be accelerated by chilling the material, such as with cold water. Other exoskeleton materials are also contemplated. For example, a plaster impregnated gauze type material may be wet, molded into place, affixed to the base or table, and allowed to cure or set. As another alternative, the exoskeleton material can be a mesh of a very stiff but pliable elastic mesh which is sufficiently stiff to hold the soft tissue substantially fixed relative to itself. Depending on the region of the anatomy, the mesh may be interconnected with more rigid plastic or other non-ferrous inserts. The inserts are preferably apertured to permit easy surgical access therethrough.

A plurality of fiducials or other markers 18 are affixed to the exoskeleton material. The fiducials carry a material which is readily detected by a magnetic resonance imaging apparatus. In one embodiment, the fiducials are hollow spheres that are filled with a material that is magnetic resonance susceptible and x-ray susceptible such that the patient can be examined by either or both x-ray or magnetic resonance techniques. A plurality of fiducials are positioned to define appropriate reference points around the region of interest. Typically, a minimum of three fiducials are adhered. Alternately, the exoskeleton material may contain magnetic resonance visible markers at relatively regular intervals. As yet another embodiment, the exoskeleton material may be itself magnetic resonance or CT imagable.

Once the fiducials are secured, such as with an adhesive, the patient support, patient, and exoskeleton are moved into a magnetic resonance imaging system 20. In the illustrated embodiment, the patient support 10 is mounted on tracks or guides for movement between poles 24 of the magnetic resonance imaging system. A magnetic resonance examination is conducted to generate magnetic resonance data which is reconstructed by a reconstruction processor 26 to form a volumetric image representation which is stored in an image memory 28. An image processor 30 selectively accesses the volumetric image memory under operator control withdraw axial, sagittal, coronal, oblique, or other slice images, as well as volume renderings, and other conventionally displayed magnetic resonance and diagnostic images. The image processor is connected with a monitor 32 such as a video monitor, LCD monitor, or gas plasma monitor.

Once the magnetic resonance examination has been completed and the volume image representation generated, the patient is prepared for a surgical procedure. The surgical procedure may be performed right in the magnetic resonance examination apparatus, adjacent the magnetic resonance apparatus, or at a remote location. Because the exoskeleton material maintains the soft tissue in a fixed position even after the patient has been moved, a high degree of freedom in moving the patient to other venues is accorded.

In the illustrated embodiment, the surgical procedure is conducted at the magnetic resonance examination site. First, the coordinate system of the electronic image representation and the coordinate system of the patient are correlated. More specifically, a wand 40 has a plurality of emitters 42 mounted thereon. Suitable emitters include light emitting diodes, lasers, ultrasonic transducers, radio transmitters, and the like. A plurality of receivers 44 are disposed adjacent to the patient. The wand 40 is positioned on each of a plurality of the fiducials 18, preferably at least three, and the emitters 42 are caused to emit. The receivers 44 receive the emitted signals and through conventional triangulation, velocity measurement, and analogous techniques, a processor 46 determines the location of the tip of the wand, hence of each fiducial in the receiver or patient coordinate system. More specifically, the processor 46 determines the location of each emitter. From the emitter locations and any offset of the emitters from the central axis, a trajectory along a central axis of the wand is determined. From the known dimensions of the wand, the location of the tip is readily determined. Alternately, an articulated, mechanical arm digitizer can be used. A coordinate system transform means 48 determines a relationship between the coordinate system of the patient and the image data.

Figure 2:
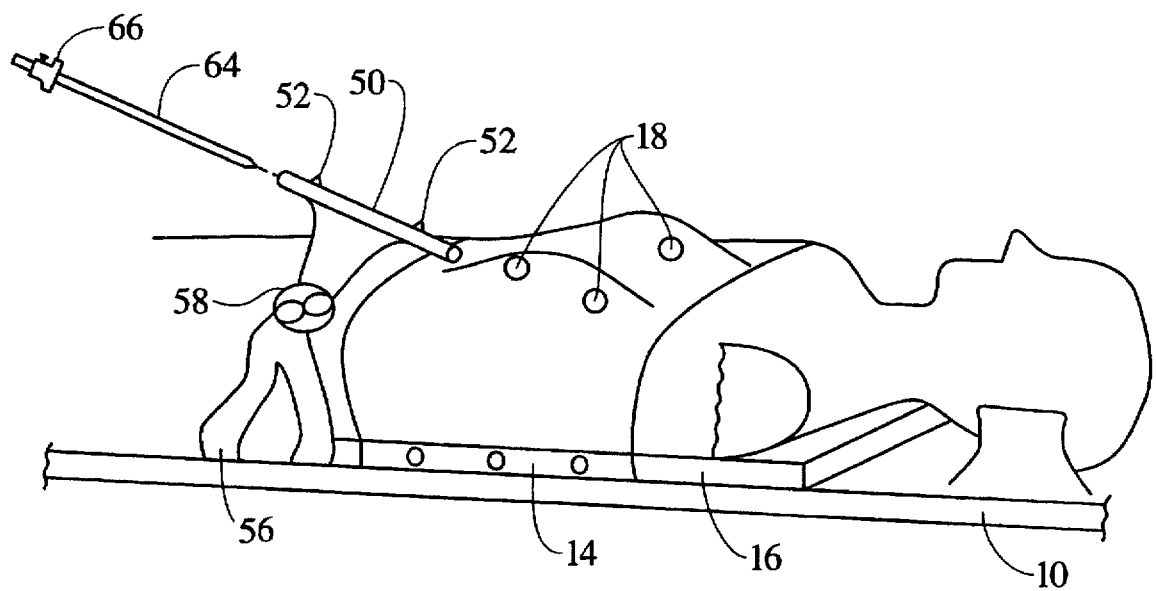

With continuing reference to FIG. 1 and further reference to FIG. 2, the location of the tumors, lesions, or other structures to be biopsied or resectioned are determined in the electronic image space. That is, the radiologist views the images on the monitor and determines the location of tumors, lesions or the like. The surgeon also views the images on the monitor and plans a surgical approach or trajectory. A stereotaxy guide, such as a needle guide 50, is mounted to the patient support, e.g., the base 16, along a generally proposed trajectory. In one embodiment, the guide has emitters 52 which are actuated. The receivers 44 receive the emitted signals from the guide. An image generator 54 causes the image processor 30 to generate an image on the monitor 32 depicting a straight line trajectory from the guide into the patient and a cross-hair referencing a preselected reference point on the guide. More specifically, the trajectory is conveyed through the transform means 48 to the image processor 30 such that the trajectory is displayed on the monitor 32 along with the cross-hair indicative of the reference point.

In another embodiment, the guide is non-ferrous and has magnetic resonance image portions, e.g., at 52, the guide is positioned in the magnetic resonance imager with the patient and an image generated. The markers appear in the displayed human-readable image. In this embodiment, the trajectory and the reference point are derived from the images of the markers at 52.

The surgeon then views a multiplicity of slices and images to determine whether the trajectory intersects the lesion, tumor, or other tissue of interest and whether the trajectory passes through the appropriate tissue. For example, the trajectory is selected to avoid major blood vessels or arteries, damaged tissue, bones, and the like. Commonly, the guide 50 is repositioned one or more times and the process repeated until a satisfactory trajectory is determined. Preferably, the guide is removably supported on a support 56 that includes lockable gimbals, hinges, or the like 58 for selectively positioning the guide 50.

Once a satisfactory trajectory is determined, the surgeon moves a cursor control, such as a mouse 60, to move a cursor display on the monitor 32. A gauging device 62 calculates a distance between the cursor controlled by the cursor control and the cross-hairs or other indicator of the reference point on the guide. The operator then selects a biopsy needle 64, or other appropriate surgical implement. A stop 66 is set in accordance with the distance between the cursor and the cross-hairs, i.e., the distance to the tumor or the like. The surgeon then inserts the biopsy needle or other surgical instrument to the appropriate depth, performs the biopsy, resection, or the like, and withdraws the needle. After the operation, the incision is closed according to conventional medical practice and the exoskeleton restraint is removed.

With non-ferrous guides and surgical instruments, the surgical procedure is performed at or in the magnetic resonance imager. Alternately, the patient and patient support can be moved to a remote site. A set of receivers 44 are disposed at the remote site for relating the coordinate system of the patient and guide at the remote site to the coordinate system of the images.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A stereotactic breast surgery method comprising:

stretching and conforming a stretchable non-ferrous exoskeleton material to a breast of a patient who is supported by a patient support;

fixing the exoskeleton material relative to the patient support such that the breast is constrained against movement;

affixing magnetic resonance markers to the exoskeleton material;

positioning at least the breast of the patient, the patient support, and the exoskeleton material in a magnetic resonance imaging system;

generating a volumetric electronic image representation with the magnetic resonance imaging system;

converting selected portions of the volumetric electronic image representation to a human-readable display of at least the breast and the markers;

establishing a relationship between a coordinate system of the human-readable displays of the volumetric electronic image representation and a coordinate system of the patient's breast and the exoskeleton material;

positioning a guide for defining a trajectory along which a surgical instrument is to be inserted through the exoskeleton material into the breast;

generating a human-readable display of the trajectory superimposed on the human-readable display of the selected portions of the volumetric electronic image representation;

adjusting the trajectory toward intersecting a selected internal region of the breast;

generating a human-readable display of the adjusted trajectory superimposed on the human-readable display of the selected portions of the volumetric electronic image representation;

checking the trajectory to be sure it (1) intersects the selected region and (2) avoids regions that would be damaged by the surgical instrument passing therethrough;

inserting the surgical instrument along the adjusted trajectory;

removing at least a portion of the selected interior region in performing at least one of a biopsy and a resection;

withdrawing the surgical instrument.

2. The method as set forth in claim 1 further including causing the stretchable exoskeleton material to set to a relatively rigid state after conforming the exoskeleton material to the breast.

3. The method as set forth in claim 2 further including prior to stretching and conforming the exoskeleton material, temporarily softening the exoskeleton material.

4. The method as set forth in claim 1 further including prior to inserting the surgical instrument, removing a portion of the exoskeleton material adjacent the trajectory.

5. The method as set forth in claim 1 wherein the exoskeleton material has a plurality of apertures therethrough and wherein the trajectory defining step includes defining a trajectory through one of the exoskeleton material apertures.

6. The method as set forth in claim 1 wherein the exoskeleton material is a thermoplastic mesh, and further including:

prior to the stretching and conforming step, heat softening the thermoplastic mesh and cooling the heat softened thermoplastic mesh below human body temperature; and after the stretching and conforming step, causing the thermoplastic material to set to a stiff, relatively rigid state.

7. A stereotaxy method comprising:

applying and conforming a stretchable non-ferrous material to a soft tissue patient portion which lacks a shape defining skeleton;

fixing the stretchable non-ferrous material relative to a support which supports at least a portion of the patient adjacent to the soft tissue such that the patient soft tissue is constrained against movement;

affixing markers to the material;

positioning at least the soft tissue portion of the patient, and exoskeleton material in a non-invasive diagnostic imaging system;

generating a volumetric electronic image representation with the non-invasive diagnostic imaging system;

converting selected portions of the volumetric electronic image representation to a human-readable display of the soft tissue portion and the markers;

positioning a guide for defining a trajectory along which a surgical instrument is to be inserted through the exoskeleton material into the soft tissue portion of the patient;

inserting the surgical instrument along the trajectory.

8. The method as set forth in claim 7 wherein the exoskeleton material is a thermoplastic mesh, and further including:

prior to the applying and conforming step, heat softening the thermoplastic mesh and cooling the heat softened thermoplastic mesh below human body temperature; and after the applying and conforming step, causing the thermoplastic material to set to a stiff, relatively rigid state.

9. The method as set forth in claim 8 further including moving the patient to a remote site before the step of inserting the surgical instrument.

10. The method as set forth in claim 8 wherein the non-invasive diagnostic imaging system is a magnetic resonance imaging system and wherein the guide and the surgical instrument are non-ferrous and wherein the step of inserting the surgical instrument is performed in the magnetic resonance imaging system.

11. The method as set forth in claim 10 wherein the guide has at least portions which are imagable in a magnetic resonance imaging machine and further including imaging the guide along with the soft tissue portion of the patient to establish a relationship between a coordinate system of the human-readable display and a coordinate system of the soft tissue portion of patient and the guide.

* * * * *